US009192200B2

(12) United States Patent
Matsuo et al.

(10) Patent No.: US 9,192,200 B2
(45) Date of Patent: Nov. 24, 2015

(54) FOOT JOINT SUPPORTER

(75) Inventors: Kazuhiko Matsuo, Tokyo (JP);
Hidefumi Koga, Gose (JP)

(73) Assignee: Kowa Company, Ltd. (JP)

( * ) Notice: Subject to any disclaimer, the term of this patent is extended or adjusted under 35 U.S.C. 154(b) by 357 days.

(21) Appl. No.: 13/522,655

(22) PCT Filed: Jan. 24, 2011

(86) PCT No.: PCT/JP2011/051219
§ 371 (c)(1),
(2), (4) Date: Jul. 17, 2012

(87) PCT Pub. No.: WO2011/090193
PCT Pub. Date: Jul. 28, 2011

(65) Prior Publication Data
US 2012/0283611 A1 Nov. 8, 2012

(30) Foreign Application Priority Data
Jan. 22, 2010 (JP) ................................. 2010-012511

(51) Int. Cl.
*A61F 13/00* (2006.01)
*A41D 13/06* (2006.01)
*A61F 13/06* (2006.01)

(52) U.S. Cl.
CPC .............. *A41D 13/06* (2013.01); *A61F 13/066* (2013.01); *A41D 2500/10* (2013.01)

(58) Field of Classification Search
CPC ..... A61D 13/06; A61F 13/066; A61F 13/064; A61F 13/065; A61F 13/061; A61F 13/08; A61F 13/00; A61F 5/0118; A61F 5/011; A61F 5/0111; A61F 5/14; A41D 13/06; A41D 2500/10; A41B 11/12; A41B 11/003

USPC ................ 602/23, 60–66, 27; 2/239–242, 61; D2/980; D24/190–192; 66/178 R
See application file for complete search history.

(56) References Cited

U.S. PATENT DOCUMENTS 1,811,786 A * 6/1931 Frei .................................. 66/187
3,386,270 A * 6/1968 Simmons ..................... 66/178 A
(Continued)

FOREIGN PATENT DOCUMENTS

JP          63-106703       7/1988
JP          11206947 A      8/1999
(Continued)

OTHER PUBLICATIONS

International Search Report of International Application No. PCT/JP2011/051219 dated Apr. 19, 2011.
(Continued)

*Primary Examiner* — Kim M Lewis
(74) *Attorney, Agent, or Firm* — Dingman, McMinnes & McLane, LLP

(57) ABSTRACT

A foot joint supporter includes a first anchor section for tightening the wearer's lower leg with a tubular knitted fabric, a second anchor section for tightening the wearer's instep and sole with the fabric, and a knitted figure eight section between the first anchor section and the second anchor section, being composed of a foot section and a body section and supporting the wearer's talocrural joint. The foot section includes an instep section covering the wearer's instep and a sole section covering the wearer's sole. A stretch resistance, in the length width direction of the tubular knitted fabric, of the sole section is larger than is the stretch resistance, in the length width direction of the tubular knitted fabric, of the instep section.

20 Claims, 12 Drawing Sheets

(56) References Cited

U.S. PATENT DOCUMENTS

| | | | | |
|---|---|---|---|---|
| 4,149,274 | A * | 4/1979 | Garrou et al. | 2/239 |
| 6,092,397 | A * | 7/2000 | Cortinovis | 66/184 |
| 6,805,681 | B2 * | 10/2004 | Yokoyama | 602/65 |
| D624,300 | S * | 9/2010 | Hollingsworth et al. | D2/980 |
| 8,495,765 | B2 * | 7/2013 | Araki et al. | 2/240 |
| 2006/0144097 | A1 * | 7/2006 | Langer et al. | 66/178 R |
| 2006/0218973 | A1 * | 10/2006 | Kim et al. | 66/178 R |
| 2007/0283483 | A1 * | 12/2007 | Jacober | 2/239 |
| 2009/0000339 | A1 * | 1/2009 | Dahlgren | 66/187 |
| 2009/0005717 | A1 * | 1/2009 | Brzank | 602/65 |
| 2009/0013450 | A1 * | 1/2009 | Lambertz | 2/239 |
| 2009/0018482 | A1 * | 1/2009 | Lambertz | 602/65 |
| 2009/0276939 | A1 | 11/2009 | Sho et al. | |
| 2010/0031706 | A1 * | 2/2010 | Chaveau et al. | 66/178 R |

FOREIGN PATENT DOCUMENTS

| | | |
|---|---|---|
| JP | 3090366 U | 12/2002 |
| JP | 2003227005 A | 8/2003 |
| JP | 3113253 U | 9/2005 |
| JP | 2007332469 A | 12/2007 |
| JP | 2008/031615 | 2/2008 |
| JP | 2008031615 A | 2/2008 |
| JP | 2008050744 | 3/2008 |
| JP | 2009179907 A | 8/2009 |

OTHER PUBLICATIONS

European Search Report of European Application No. EP 11734799. 7, Dated Dec. 12, 2013.

* cited by examiner

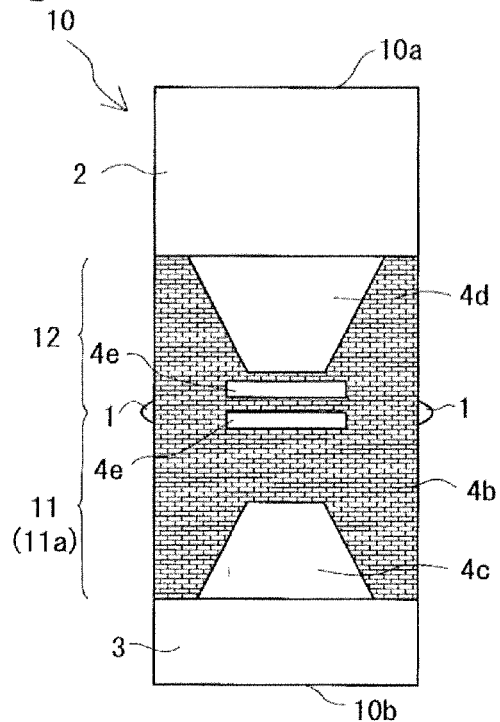
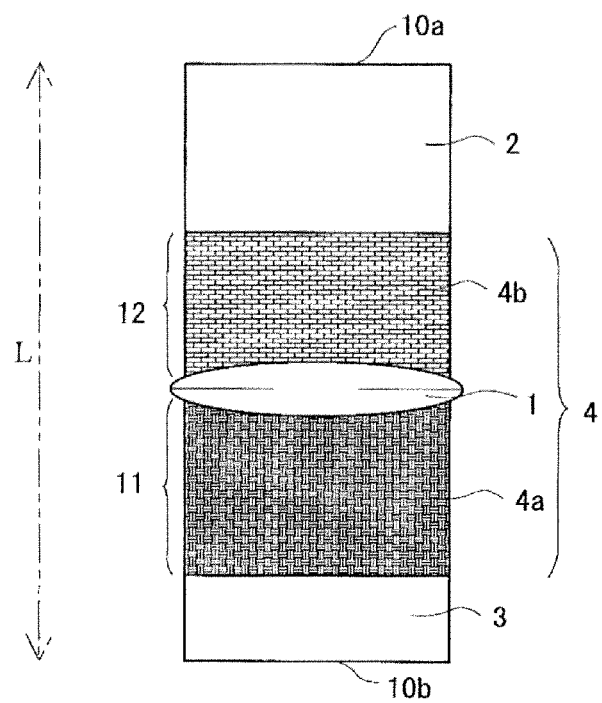
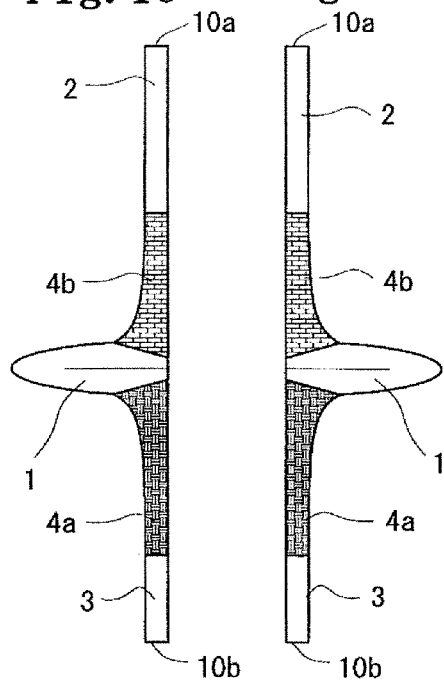
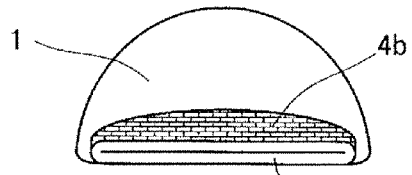
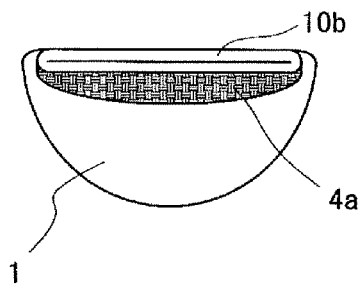

Fig. 2a    Fig. 2b    Fig. 2c
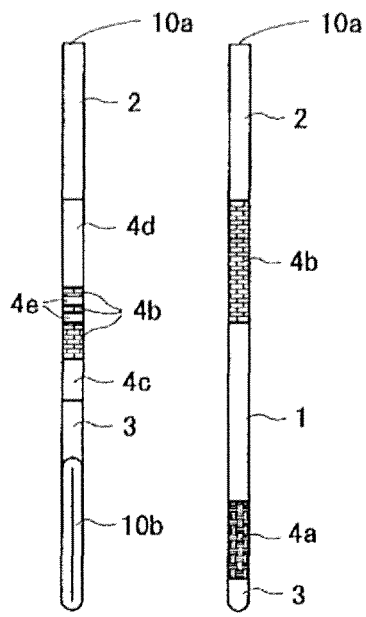
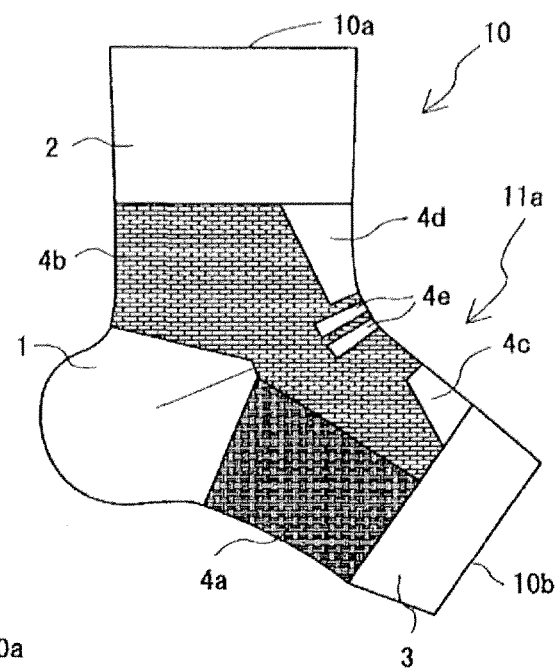
Fig. 2d
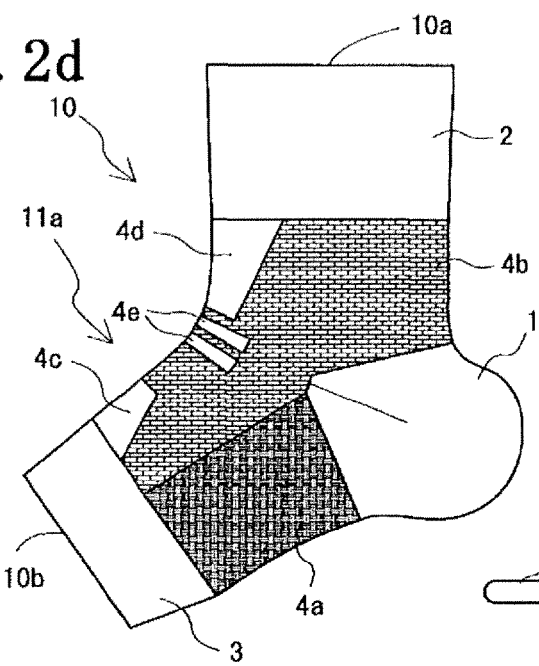
Fig. 2e
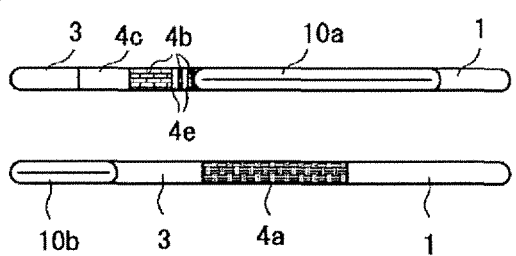
Fig. 2f

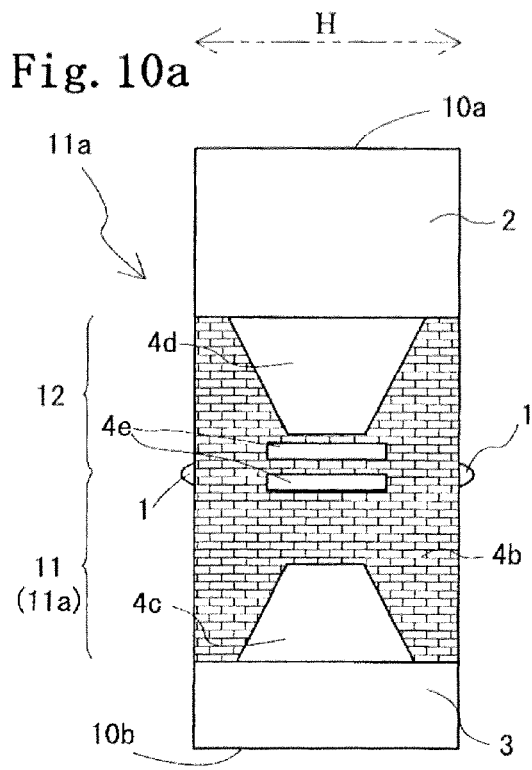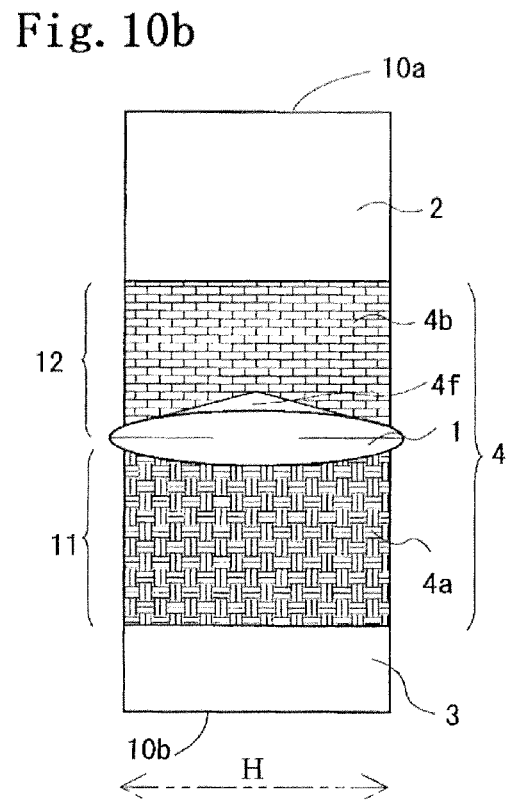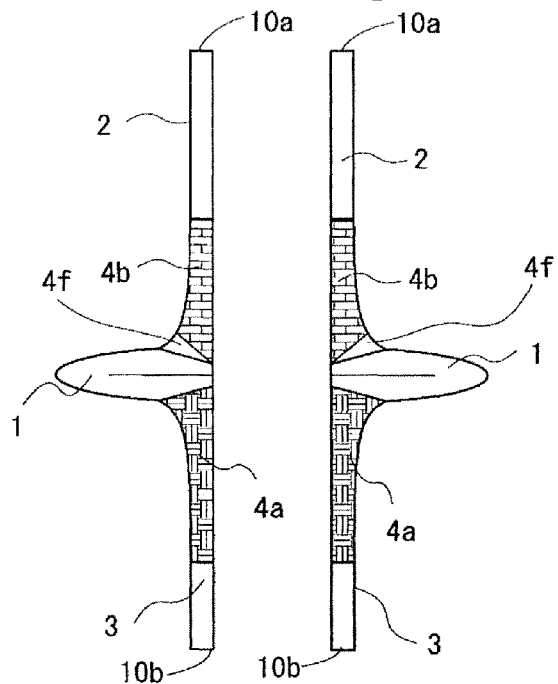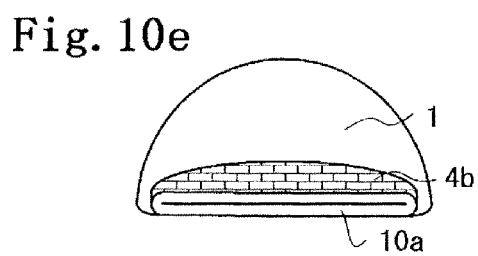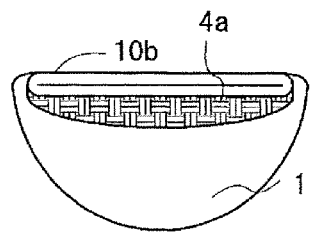
Fig. 10a  Fig. 10b  Fig. 10c  Fig. 10d  Fig. 10e  Fig. 10f

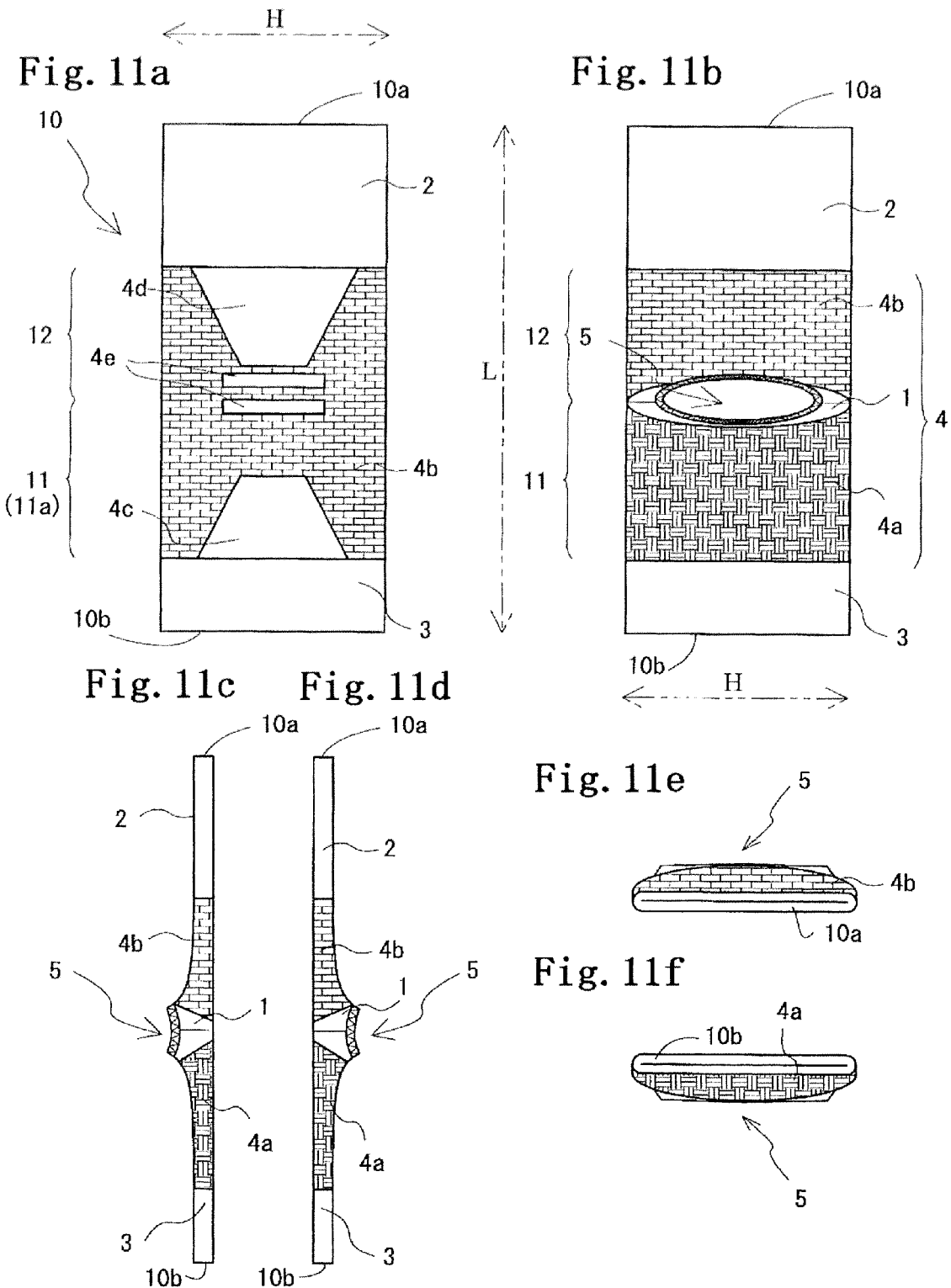

FOOT JOINT SUPPORTER

TECHNICAL FIELD

The present invention relates to a foot joint supporter which can support wearer's daily motion, and particularly, to a foot joint supporter having a taping function of improving stability of the foot joint, thereby reducing the fatigue of the triceps surae muscle (the calf) and also relieving pains of the Achilles' tendon, the triceps surae muscle, and the outside (the ligament) of the foot joint.

BACKGROUND ART

A sock or a tubular supporter for lower limb in the related art is a sock or a tubular supporter for lower limb, which covers a foot section, an ankle section, and a calf section, and has a stretchable reinforcing section integrally provided at a section covering from a sole section corresponding to the calcaneal bone and/or the cuboid bone to the side surface of the ankle section, and compression pressure distribution in which compression pressure is gradually reduced from the ankle section to the calf section when worn is provided (refer to PTL 1, for example).

CITATION LIST

Patent Literature

[PTL 1] JP-A-2007-332469

SUMMARY OF INVENTION

Technical Problem

In the sock or the tubular supporter for lower limb in the related art, a foot arch reinforcing section is provided at a position where the periphery of the foot section is covered so as to be able to press the foot arch. However, this foot arch is the tarsal arch and the foot arch reinforcing section is not provided at a position where the periphery of the foot section is covered so as to be able to press the metatarsal bone arch. That is, the sock or the tubular supporter for lower limb in the related art is for being used for improvement in performance in a sport or a fatigue reduction such as the prevention or reduction of an edema of the lower limb and is not for supporting the formation of the outer longitudinal arch and the medial longitudinal arch which are important for the support of the body weight in an ideal weight shift (three-point walking) in which the centroid of a wearer moves from the heel to the big toe of the wearer.

The present invention has been made to solve the problem as described above and has an object to provide a foot joint supporter having a taping function of pushing the plantar arch of a wearer up and supporting the formation of the medial longitudinal arch, thereby being able to enhance walking performance of the wearer.

Solution to Problem

A foot joint supporter according to the invention includes: a first anchor section which is knitted to go around one end of a tubular knitted fabric, surrounds portions corresponding to the tibia and the fibula in the vicinity of the malleolus of a wearer, and makes the tubular knitted fabric be tightened on the lower leg of the wearer; a second anchor section which is knitted to go around the other end of the tubular knitted fabric, surrounds portions corresponding to the first metatarsal bone, the second metatarsal bone, the third metatarsal bone, the fourth metatarsal bone, and the fifth metatarsal bone in the vicinity of the metatarsophalangeal joint of the wearer, and makes the tubular knitted fabric be tightened on the instep and the sole of the foot of the wearer; and a figure eight section which is knitted as a body section and a foot section excluding portions corresponding to the heel and the tiptoe of the wearer between the first anchor section and the second anchor section of the tubular knitted fabric and supports the talocrural joint of the wearer, wherein the foot section in the figure eight section includes an instep section corresponding to the instep of the foot of the wearer and a sole section corresponding to the sole of the foot of the wearer, and the stretch resistance of the sole section in a length direction of the tubular knitted fabric is larger than the stretch resistance of the instep section in the length direction of the tubular knitted fabric.

Advantageous Effects of Invention

In the foot joint supporter according to the invention, as well as pushing the plantar arch of a wearer up and supporting the formation of the medial longitudinal arch, thereby being able to enhance walking performance of the wearer, improvement in stability of the foot joint is attained, thereby reducing the fatigue of the triceps surae muscle and also relieving pains of the Achilles' tendon, the triceps surae muscle, and the outside (the ligament) of the foot joint.

BRIEF DESCRIPTION OF DRAWINGS

FIG. 1(a) is a front view showing the schematic configuration of a foot joint supporter related to the first embodiment, FIG. 1(b) is a back view of the foot joint supporter shown in FIG. 1(a), FIG. 1(c) is a left side view of the foot joint supporter shown in FIG. 1(a), FIG. 1(d) is a right side view of the foot joint supporter shown in FIG. 1(a), FIG. 1(e) is a plan view of the foot joint supporter shown in FIG. 1(a), and FIG. 1(f) is a bottom view of the foot joint supporter shown in FIG. 1(a).

FIG. 2(a) is a front view of the foot joint supporter shown in FIG. 1 when viewed from a different direction, FIG. 2(b) is a back view of the foot joint supporter shown in FIG. 2(a), FIG. 2(c) is a left side view of the foot joint supporter shown in FIG. 2(a), FIG. 2(d) is a right side view of the foot joint supporter shown in FIG. 2(a), FIG. 2(e) is a plan view of the foot joint supporter shown in FIG. 2(a), and FIG. 2(f) is a bottom view of the foot joint supporter shown in FIG. 2(a).

FIG. 10(a) is a front view showing the schematic configuration of a foot joint supporter related to the second embodiment, FIG. 10(b) is a back view of the foot joint supporter shown in FIG. 10(a), FIG. 10(c) is a left side view of the foot joint supporter shown in FIG. 10(a), FIG. 10(d) is a right side view of the foot joint supporter shown in FIG. 10(a), FIG. 10(e) is a plan view of the foot joint supporter shown in FIG. 10(a), and FIG. 10(f) is a bottom view of the foot joint supporter shown in FIG. 10(a).

FIG. 11(a) is a front view showing the schematic configuration of a foot joint supporter related to the third embodiment, FIG. 11(b) is a back view of the foot joint supporter shown in FIG. 11(a), FIG. 11(c) is a left side view of the foot joint supporter shown in FIG. 11(a), FIG. 11(d) is a right side view of the foot joint supporter shown in FIG. 11(a), FIG. 11(e) is a plan view of the foot joint supporter shown in FIG. 11(a), and FIG. 11(f) is a bottom view of the foot joint supporter shown in FIG. 11(a).

DESCRIPTION OF EMBODIMENTS (First Embodiment of the Invention)

Figure 3A:
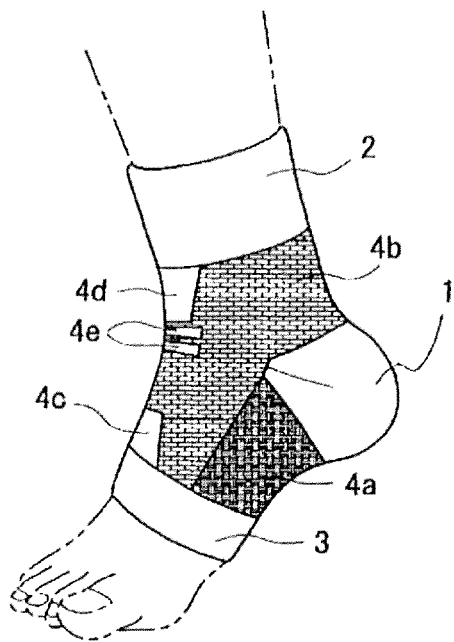
FIG. 3(a) is a right side view showing a wearing state of the foot joint supporter shown in FIGS. 1 and 2.
Figure 3C:
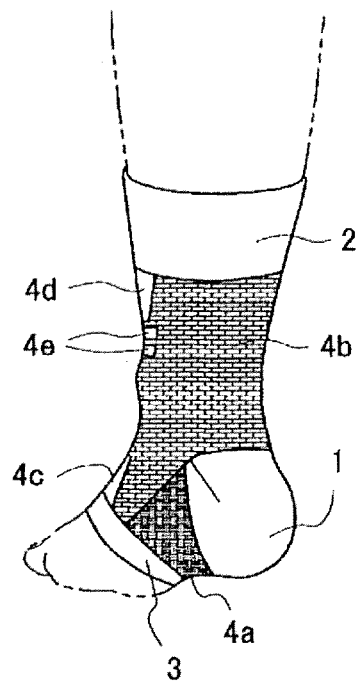
FIG. 3(c) is a perspective view showing a wearing state of the foot joint supporter shown in FIGS. 1 and 2 when viewed from the right rear side.
Figure 3B:
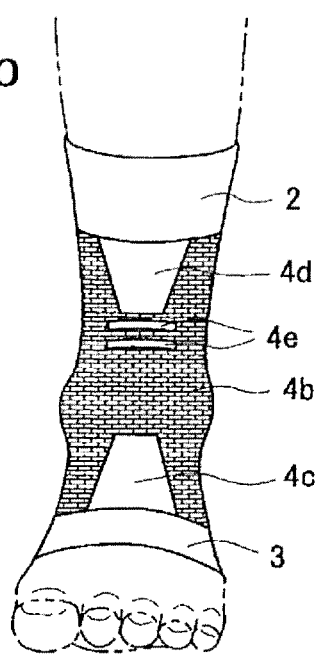
FIG. 3(b) is a front view showing a wearing state of the foot joint supporter shown in FIGS. 1 and 2.

In FIGS. 1 to 3, a foot joint supporter 10 is made of a tubular knitted fabric which is knitted in circular knitting by a hosiery knitting machine (for example, a type of knitting machine (number of needles: 256) manufactured by Lonati Co. and is a supporter which comes into close contact with the body surface of a wearer, thereby assisting the foot joint of the wearer.

The foot joint supporter 10 has a desired functionality such as a taping function by performing different knitting with respect to a base fabric section 1 that is a stretchable knitted fabric which is knitted in a plain stitch, a rib stitch, a tuck at itch, a float stitch, a pile stitch, or the like by using an upper thread, an under thread, and a rubber thread as knitting yarn. In addition, the base fabric section 1 related to this embodiment is a heel shaping section corresponding to the heel of a wearer, and is a knitted fabric which is knitted in a plain stitch (hereinafter referred to as a plain stitch knitted fabric).

Further, the foot joint supporter 10 has a first anchor section 2 which is knitted to go around one end (an upper end 10a) of the tubular knitted fabric, surrounds portions corresponding to the tibia and the fibula in the vicinity of the malleolus of a wearer, and makes the foot joint supporter 10 be tightened on the lower leg of the wearer, and a second anchor section 3 which is knitted to go around the other end (a lower end 10b) of the tubular knitted fabric, surrounds portions corresponding to the first metatarsal bone, the second metatarsal bone, the third metatarsal bone, the fourth metatarsal bone, and the fifth metatarsal bone in the vicinity of the metatarsophalangeal joint of the wearer, and makes the foot joint supporter 10 be tightened on the instep and the sole of the foot of the wearer.

The first anchor section 2 and the second anchor section 3 are knitted such that the stretch resistance thereof in a circumferential direction H of the foot joint supporter 10 (the tubular knitted fabric) is larger than the stretch resistance of the base fabric section 1 in the circumferential direction H of the foot joint supporter 10. That is, when tension in a case where certain elongation has been imparted from a state where elongation is not imparted to a material is set to be F, the tension of the base fabric section 1 in the circumferential direction H of the foot joint supporter 10 is set to be $F_{H1}$, the tension of the first anchor section 2 in the circumferential direction H of the foot joint supporter 10 is set to be $F_{H2}$, and the tension of the second anchor section 3 in the circumferential direction H of the foot joint supporter 10 is set to be $F_{H3}$, the first anchor section 2 and the second anchor section 3 have such a magnitude relation of $F_{H2} \approx F_{H3} > F_{H1}$ that they have strong tightening forces in the circumferential direction H of the foot joint supporter 10, compared to the base fabric section 1.

Specifically, by making each of the first anchor section 2 and the second anchor section 3 be a knitted fabric knitted in a moss stitch (hereinafter referred to as a moss stitch knitted fabric), it is possible to make the stretch resistance thereof in the circumferential direction H of the foot joint supporter 10 large with respect to the base fabric section 1 that is the plain stitch knitted fabric.

In addition, the moss stitch knitted fabric is a knitted fabric in which a plain stitch and a tuck (a structure in which no loop protrudes over a certain course and plural loops protrude over the subsequent course) appear alternately or for every few courses in the course direction and the wale direction. For this reason, in the first anchor section 2 and the second anchor section 3, the plain stitch and the tuck are used in combination, whereby it is possible to make protuberances or openwork stitches on the surface of a knitted fabric and a mesh pattern such as a moss appears.

In this manner, the first anchor section 2 is knitted to surround the lower leg of a wearer and the stretch resistance of the first anchor section 2 in the circumferential direction H of the foot joint supporter 10 is larger than the stretch resistance of the base fabric section 1 in the circumferential direction H of the foot joint supporter 10, whereby it is possible to fix the foot joint supporter 10 to the lower leg of a wearer and suppress slipping-off of the upper end 10a of the foot joint supporter 10 at the time of the dorsal flexion of the foot joint. Further, the first anchor section 2 is connected to a figure eight section 4 (described later), thereby also functioning as an anchor of the figure eight section 4.

Further, the second anchor section 3 is knitted to surround the instep and the sole of the foot of a wearer, and the stretch resistance of the second anchor section 3 in the circumferential direction H of the foot joint supporter 10 is larger than the stretch resistance of the base fabric section 1 in the circumferential direction H of the foot joint supporter 10, whereby it is possible to fix the foot joint supporter 10 to the instep and the sole of the foot of a wearer and suppress slipping-off of the lower end 10b of the foot joint supporter 10 at the time of the dorsal flexion of the foot joint. Further, the second anchor section 3 is connected to the figure eight section 4 (described later), thereby also functioning as an anchor of the figure eight section 4.

In addition, if tightening forces on the lower leg and the instep and the sole of the foot of a wearer by the first anchor section 2 and the second anchor section 3 are too strong, constriction of blood flow in the lower leg and the instep and the sole of the foot occurs, thereby causing a feeling of discomfort to a wearer. In particular, the feeling of discomfort is remarkable in the lower leg, compared to the instep and the sole of the foot.

For this reason, in the foot joint supporter 10 related to this embodiment, the feeling of discomfort which is imparted to a wearer is alleviated by widening the area of the first anchor section 2 which comes into contact with the body surface of a wearer, with respect to the second anchor section 3, thereby dispersing pressure which is applied to the body surface by the first anchor section 2, and also adjusting density in a portion of the first anchor section 2 for example, to make a tightening force thereof small by about 10% with respect to the second anchor section 3). That is, it is preferable that the foot joint supporter 10 related to this embodiment have a magnitude relation of $F_{H3} > F_{H2} > F_{H1}$ so as to have a moderate tightening force in the circumferential direction H of the foot joint supporter 10.

The figure eight section 4 is knitted as a body section 12 and a foot section 11 excluding portions corresponding to the heel and the tiptoe of a wearer between the first anchor section 2 and the second anchor section 3 of the foot joint supporter 10 and supports the talocrural joint of the wearer. Further, the figure eight section 4 is locked at the first anchor section 2 on the lower leg side of a wearer and locked at the second anchor section 3 on the foot side of the wearer.

The figure eight section 4 wraps up the talocrural joint of a wearer, establishes joint compatibility, stabilizes the foot joint, and suppresses (heel locking) deflection of the ankle of the wearer at the time of walking, thereby preventing varus sprain or eliminating instability or the like at the time of standing on one leg, so that it is possible to assist stable walking of the wearer.

Figure 4A:
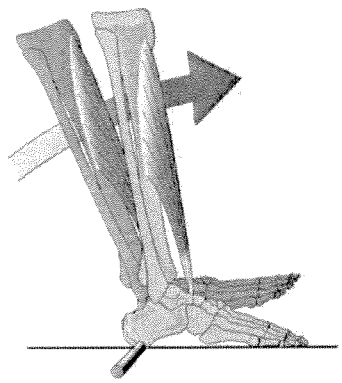
FIG. 4(a) is an explanatory diagram for describing an impact absorption action by the gastrocnemius in an initial stage of a stance phase.
Figure 4B:
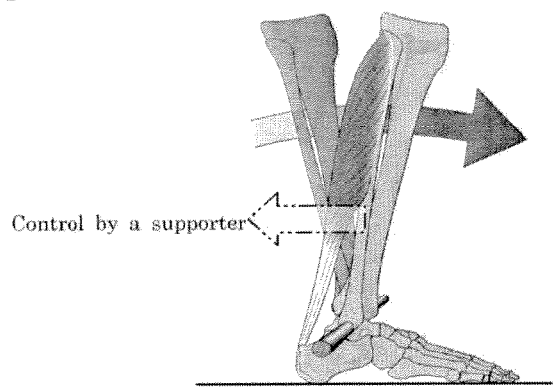
FIG. 4(b) is an explanatory diagram for describing the braking on the front side of the lower leg by the triceps surae muscle in an intermediate stage of the stance phase.
Figure 4C:
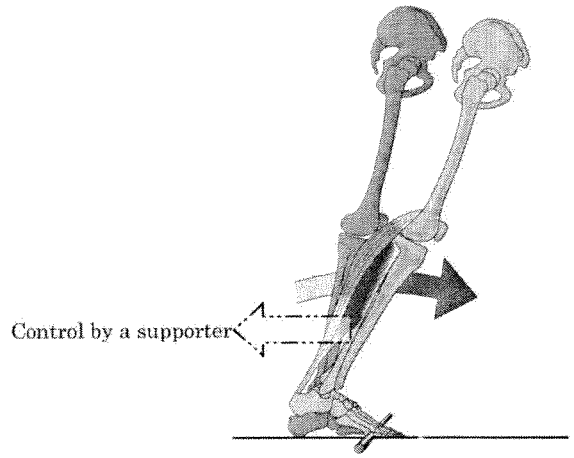
FIG. 4(c) is an explanatory diagram for describing a propulsive force action by the triceps surae muscle in a late stage of the stance phase.

Here, as shown in FIG. 4, the function of the triceps surae muscle is principal over a stage from an intermediate stage (FIG. 4(b)) to a late stage (FIG. 4(c)) of a stance phase (a period where the foot is grounded during walking).

For this reason, the figure eight section 4 performs the dorsal flexion braking of the foot joint by a taping function from the calcaneus to the Achilles' tendon of a wearer, thereby being able to reduce a burden to the lower leg over a stage from the intermediate stage to the late stage of the stance phase and also perform assistance of takeoff (a propulsive force in walking) from the late stage of the stance phase.

Further, the figure eight section 4 assists the dorsal flexion braking of the foot joint, thereby being able to lead the centroid of a wearer in a tiptoe direction and assist walking of the wearer. Further, the figure eight section 4 can stabilize the foot joint of a wearer and performs assistance for absorbing an impact from the ground (a floor) in an initial stage (FIG. 4(a)) of the stance phase.

In particular, the foot section 11 in the figure eight section 4 is composed of an instep section 11a corresponding to the instep of the foot of a wearer and a sole section 4a corresponding to the sole of the foot of the wearer, and is knitted such that the stretch resistance of the sole section 4a in a length direction L of the foot joint supporter 10 is larger than the stretch resistance of the instep section 11a in the length direction L of the foot joint supporter 10.

Further, the instep section 11a in the figure eight section 4 is provided with an approximately trapezoidal first buffer section 4c which is knitted in different knitting on the second anchor section 3 side of the foot joint supporter 10 such that the stretch resistance of an area knitted in the different knitting in the length direction L of the foot joint supporter 10 is smaller than the stretch resistance of the other area in the instep section 11a.

Further, the body section 12 in the figure eight section 4 is provided with an approximately trapezoidal second buffer section 4d which is knitted in different knitting on the front face side of the foot joint supporter 10 such that the stretch resistance of an area knitted in the different knitting in the length direction L of the foot joint supporter 10 is smaller than the stretch resistance of the other area in the body section 12.

In addition, in this embodiment, the other area in the instep section 11a and the other area in the body section 12 are a continuous knitted fabric (hereinafter referred to as a supporting section 4b) and are made of a knitted fabric in which a 2×1 tuck stitch and a plating stitch are used in combination (hereinafter referred to as a 2-tuck stitch-plating stitch knitted fabric).

Further, in this embodiment, the sole section 4a is made of a knitted fabric in which a 1×1 tuck stitch and a plating stitch are used in combination (hereinafter referred to as a 1-tuck stitch-plating stitch knitted fabric), and each of the first buffer section 4c and the second buffer section 4d is made of a knitted fabric which is knitted in a 2×1 tuck stitch (hereinafter referred to as a 2-tuck stitch knitted fabric).

Here, a tuck stitch knitted fabric is a knitted fabric in which a certain loop is not made temporarily when knitting the fabric and loops are made together when knitting the next course. In addition, in this embodiment, in consideration of a balance with density, the number of times to tuck as the knitted fabrics of the supporting section 4b, the first buffer section 4c, and the second buffer section 4d is set to be twice, and the number of times to tuck as the knitted fabric of the sole section 4a is set to be once. However, as long as a desired difference in stretch resistance can be obtained, the number of times is not limited thereto.

Further, in a tuck stitch-plating stitch knitted fabric, expansion and contraction of the sole section 4a and the supporting section 4b in the length direction L of the foot joint supporter 10 is moderately suppressed by additionally feeding another knitting yarn (for example, woolly nylon yarn) in addition to the ground knitting yarn of the tuck stitch. That is, in the tuck stitch-plating stitch knitted fabric, knitting is performed such that elongation in the length direction L of the foot joint supporter 10 is small compared to elongation in the circumferential direction H. Further, in the tuck stitch-plating stitch knitted fabric, another knitting yarn is cut at the boundary between the sole section 4a and the supporting section 4b and the other area (cut boss).

In this manner, by making the sole section 4a be the 1-tuck stitch-plating stitch knitted fabric, making the supporting section 4b be the 2-tuck stitch-plating stitch knitted fabric, and making the first buffer section 4c be the 2-tuck stitch knitted fabric, it is possible to make the stretch resistance of the sole section 4a in the length direction L of the foot joint supporter 10 large with respect to the instep section 11a.

Further, by making the supporting section 4b be the 2-tuck stitch-plating stitch knitted fabric and making the second buffer section 4d be the 2-tuck stitch knitted fabric, it is possible to make the stretch resistance of the second buffer section 4d in the length direction L of the foot joint supporter 10 small with respect to the supporting section 4b in the body section 12.

That is, when the tension of the supporting section 4b in the length direction L of the foot joint supporter is set to be $F_{L4b}$, the tension of the first buffer section 4c in the length direction L of the foot joint supporter 10 is set to be $F_{L4c}$, and the tension of the second buffer section 4d in the length direction L of the foot joint supporter 10 is set to be $F_{L4d}$, the supporting section 4b has such a magnitude relation of $F_{L4b}>F_{L4c}\approx F_{L4d}$ that it has a strong tightening force in the length direction L of the foot joint supporter 10, compared to the first buffer section 4c and the second buffer section 4d.

Further, when the tension of the sole section 4a in the length direction L of the foot joint supporter 10 is set to be $F_{L4a}$, the sole section 4a has such a magnitude relation of $F_{L4a}>F_{L4b}>F_{L4c}$ that it has a strong tightening force in the length direction L of the foot joint supporter 10, compared to the instep section 11a.

In this manner, the sole section 4a eliminates elongation in the course direction, thereby supporting the formation of the medial longitudinal arch (an arch including the calcaneus, the talus, the navicular bone, the first cuneiform bone, the first metatarsal bone, and the phalanx as component bones) of a wearer, and being able to push the plantar arch of the wearer up, so that it is possible to make it easy for the wearer to walk.

Further, the first buffer section 4c weakens a tightening force on the second anchor section 3 side on the supporting section 4b in the instep section 11a, thereby making a force of pushing the plantar arch of a wearer up by the sole section 4a act obliquely upward on the second anchor section 3 side, rather than vertically upward with respect to the sole section 4a, and suppresses landing of the tiptoe of the wearer at an acute angle with respect to the ground, thereby being able to prevent a misstep during walking of the wearer.

Further, the second buffer section 4d weakens tightening force on the supporting section 4b on the front face side of the body section 12 and makes the supporting section 4b not go around the tubular knitted fabric on the first anchor section 2 side, thereby suppressing tightening on the Achilles' tendon of a wearer while maintaining a tightening force on the ankle by the figure eight section 4, so that it is possible to relieve pain.

In addition, in this embodiment, the first buffer section 4c and the second buffer section 4d are set to be the 2-tuck stitch knitted fabric. However, a knitted fabric knitted in a mesh stitch that is a knitting structure having good air permeability and a small stretching force (hereinafter referred to a mesh stitch knitted fabric) is also acceptable. In this way, the first buffer section 4c and the second buffer section 4d emphasize contrast between the strength and the weakness of the knitted fabrics of the supporting section 4b and the sole section 4a which are adjacent to the first buffer section 4c and the second buffer section 4d, so that it is possible to make a wearer further really feel a taping effect by the figure eight section 4.

A thinly knitted section 4e is a knitted fabric which is composed of ground knitting yarn without feeding another knitting yarn, in the vicinity of the boundary between the body section 12 and the foot section 11 in the figure eight section 4 on the front face side of the foot joint supporter 10, is an area extending the circumferential direction H of the foot joint supporter 10, and is made to be thin in thickness with respect to the thickness of the knitted fabric in the supporting section 4b.

In addition, since the supporting section 4b is a knitted fabric which is composed of the 2-tuck stitch-plating stitch knitted fabric, the knitted fabric becomes thick compared to normal socks, so that the supporting section 4b is not smoothly bent at a bent portion (the front face side of the ankle of a wearer) of the foot joint supporter 10, thereby causing wrinkles. In order to prevent occurrence of the wrinkles, originally, it is good to make the knitted fabric of the entire bent portion of the foot joint supporter 10 thin. However, if the knitted fabric of the entire bent portion of the foot joint supporter 10 is made thin, it does not become possible to maintain a tightening force on the ankle by the figure eight section 4.

For this reason, by making the thinly knitted section 4e be an area extending the circumferential direction H at a portion of the supporting section 4b, it is possible to avoid occurrence of the wrinkles in the bent portion of the foot joint supporter 10 while maintaining a tightening force on the ankle by the figure eight section 4. In addition, in FIGS. 1 to 3, a case where two thinly knitted section 4e are arranged in parallel in the length direction L is shown. However, as long as occurrence of wrinkles in the bent portion of the foot joint supporter 10 can be prevented, the number thereof is not limited thereto.

In addition, by making the thinly knitted section 4e related to this embodiment be a mesh stitch knitted fabric, it is possible to make the stretch resistance thereof in the length direction L of the foot joint supporter 10 small with respect to the base fabric section 1 that is the plain stitch knitted fabric. The mesh stitch knitted fabric is a knitted fabric in which a certain loop is not made temporarily when knitting the fabric and loops are made together when knitting the next course and which stretches well with knitting in the form of a mesh.

In particular, when the tension of the thinly knitted section 4e in the length direction L of the foot joint supporter 10 is set to be $F_{L4e}$, the thinly knitted section 4e has such a magnitude relation of $F_{L1}>F_{L4e}$, that it has a weak tightening force in the length direction L of the foot joint supporter 10, compared to the base fabric section 1.

In addition, in the foot joint supporter 10 related to this embodiment, due to the knitted fabric of each site described above, the stretch resistances of the first buffer section 4c and the second buffer section 4d in the length direction L of the foot joint supporter 10 are larger than the stretch resistance of the second anchor section 3 in the length direction L of the foot joint supporter 10. Further, the stretch resistance of the second anchor section 3 in the length direction L of the foot joint supporter 10 is larger than the stretch resistance of the first anchor section 2 in the length direction L of the foot joint supporter 10. Further, the stretch resistance of the first anchor section 2 in the length direction of the foot joint supporter 10 is larger than the stretch resistance of the base fabric section 1 in the length direction L of the foot joint supporter 10.

Therefore, the foot joint supporter 10 related to this embodiment satisfies a magnitude relation shown by the following expression (1) in the tension F in the length direction L of the foot joint supporter 10. However, in the following expression (1), $F_{L4c}$ is the tension of the first buffer section 4c in the length direction L of the foot joint supporter 10, $F_{L4d}$ is the tension of the second buffer section 4d in the length direction L of the foot joint supporter 10, $F_{L2}$ is the tension of the first anchor section 2 in the length direction L of the foot joint supporter 10, and $F_{L3}$ is the tension of the second anchor section 3 in the length direction L of the foot joint supporter 10.

[Expression 1]

$$F_{L4a}>F_{L4b}>F_{L4c}\approx F_{L4d}>F_{L3}>F_{L2}>F_{L1}>F_{L4e} \quad (1)$$

In addition, in this embodiment, as the ground knitting yarn which is used in the plain stitch, the moss stitch, the tuck stitch, and the mesh stitch, an upper thread which is nylon yarn having a thickness of 70 deniers and is composed of two pieces of knitting yarn, an under thread which is nylon yarn having a thickness of 30 deniers and is composed of two pieces of knitting yarn, and a rubber thread which is covering yarn (DCY: double covered yarn) in which two pieces of nylon winding yarn each having a thickness of 40 deniers are wound around polyurethane core yarn having a thickness of 260 deniers are used. However, the threads are not limited to these materials.

For example, as the upper thread, it is preferable to select a natural fiber such as cotton, wool (cashmere, lamb, Angora, or the like), silk, or hemp, a chemical fiber such as acrylic, a material having a sweat absorbing, quick-drying, or body temperature adjusting function, or the like according to the cost of the foot joint supporter 10 or the needs of a wearer. Further, as the under thread, it is preferable to select an ester, FTY (filament twisted yarn), or an antibacterial, deodorant, or odor eliminating material according to the cost of the foot joint supporter 10 or the needs of a wearer.

Further, the woolly nylon yarn (pattern yarn) in the 1-tuck stitch-plating stitch knitted fabric (the sole section 4a) and the 2-tuck stitch-plating stitch knitted fabric (the supporting section 4b) is composed of two pieces of knitting yarn each having a thickness of 100 deniers.

Figure 5:
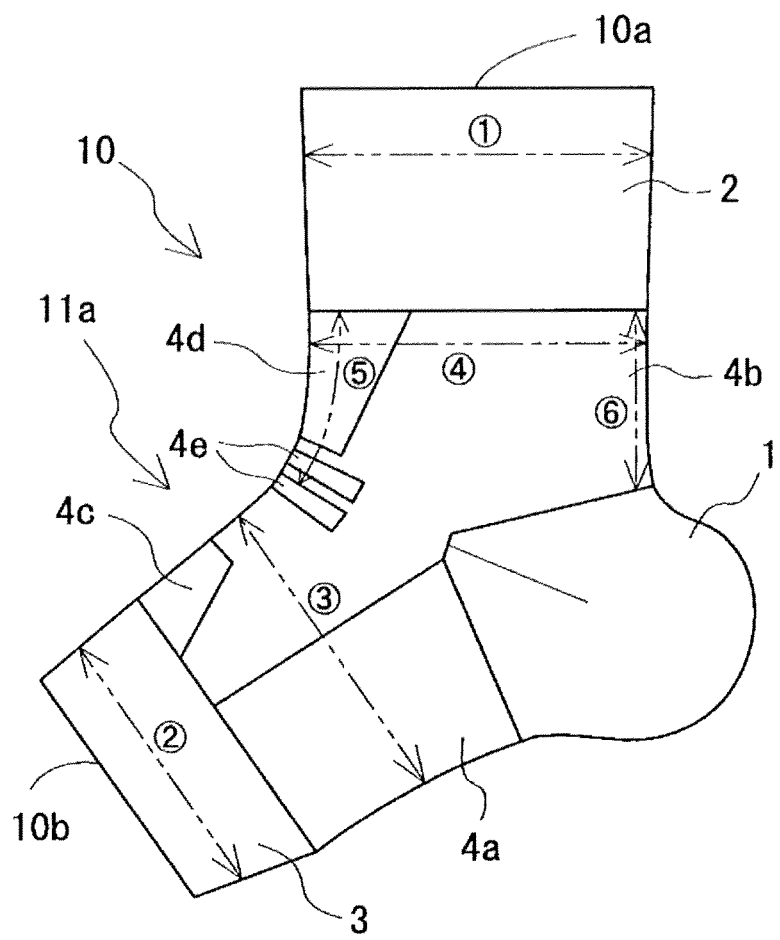
FIG. 5 is an explanatory diagram for describing sites for measuring an elongation rate in the foot joint supporter shown in FIG. 1(d).

Here, the results of measurement of an elongation rate (the percentage of a difference between a length when elongated (an elongated dimension) and the original length (the original dimension) to the original length) measured with respect to the respective site (refer to FIG. 5) of the foot joint supporter 10 made according to the above-described knitting yarn and knitted fabrics by using a stretch tester (tensile load: 4 kg) are shown in Table 1 below.

TABLE 1

| Measured site | | Original dimension [cm] | Elongated dimension [cm] | Elongation rate [%] |
|---|---|---|---|---|
| Circled number 1 | Circumferential direction H of the first anchor section 2 | 8.5 | 25.0 | 194.1 |
| Circled number 2 | Circumferential direction H of the second anchor section 3 | 8.6 | 22.5 | 161.6 |
| Circled number 3 | Circumferential direction H over the sole section 4a and the supporting section 4b in the foot section 11 | 8.6 | 18.0 | 109.3 |
| Circled number 4 | Circumferential direction H over the supporting section 4b and the second buffer section 4d in the body section 12 | 8.5 | 19.0 | 123.5 |
| Circled number 5 | Length direction L over the supporting section 4b, the second buffer section 4d, and the thinly knitted section 4e between the | 5.7 | 12.5 | 119.3 |

TABLE 1-continued

| Measured site | | Original dimension [cm] | Elongated dimension [cm] | Elongation rate [%] |
|---|---|---|---|---|
| | bend portion of the foot joint supporter 10 and the first anchor section 2 | | | |
| Circled number 6 | Length direction L of the supporting section 4b in the body section 12 | 5.7 | 10.0 | 75.4 |

In addition, since the elongation rate in Table 1 represents the fact that the larger the value, the more easily the knitted fabric is elongated and the tension F in the above-described expression (1) represents the fact that the larger the value, the more difficult it is for the knitted fabric to be elongated (the larger the tightening force), an inequality sign showing the magnitude relation of the elongation rate and an inequality sign showing the magnitude relation of the tension F become opposite to each other.

Next, the result of verification of the operation and effects of the foot joint supporter 10 related to this embodiment will be described.

In the first experiment, in a case where the foot joint supporter 10 is worn on the right ankle of a test subject (a 26-years-old healthy male, there is no anamnesis in four limbs) (hereinafter referred to as the time of wearing) and a case where the foot joint supporter 10 is not worn (hereinafter referred to as the time of non-wearing), free walking was carried out 10 times and changes in the angle of the foot joint and foot joint moments were compared by three-dimensional motion analysis. In addition, in the three-dimensional motion analysis, a three-dimensional motion analysis system "VICON MX" manufactured by VICON, Inc. was used.

Figure 6A:
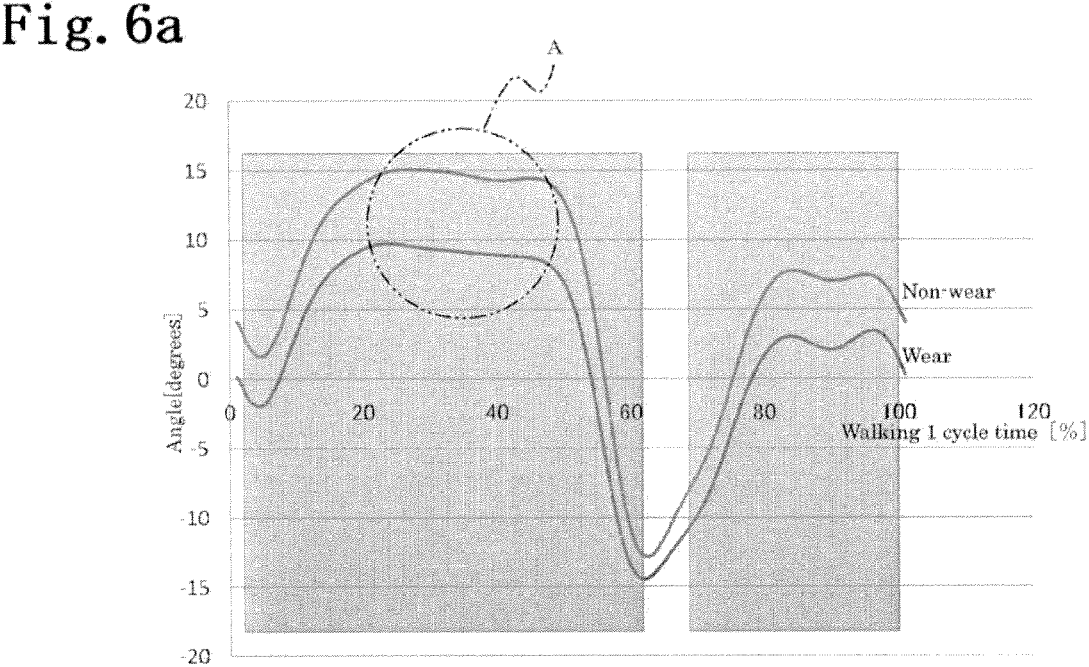
FIG. 6(a) is a graph showing the measurement results of a foot joint angle by three-dimensional motion analysis for verifying the operation and effects of the foot joint supporter shown in FIG. 1.

As shown in FIG. 6(a), it can be found that the angle of the foot joint at the time of wearing significantly increases in almost the entire period of a stance phase, compared to the angle of the foot joint at the time of non-wearing.

In particular, in a period A shown by a two-dot chain line in FIG. 6(a), it can be found that a dorsal flexion angle at the time of wearing increases, so that a wearer can lean against the foot joint supporter 10 with respect to a dorsal flexion direction, and the effect of assisting the muscle (the triceps surae muscle) of the wearer is high.

Figure 6B:
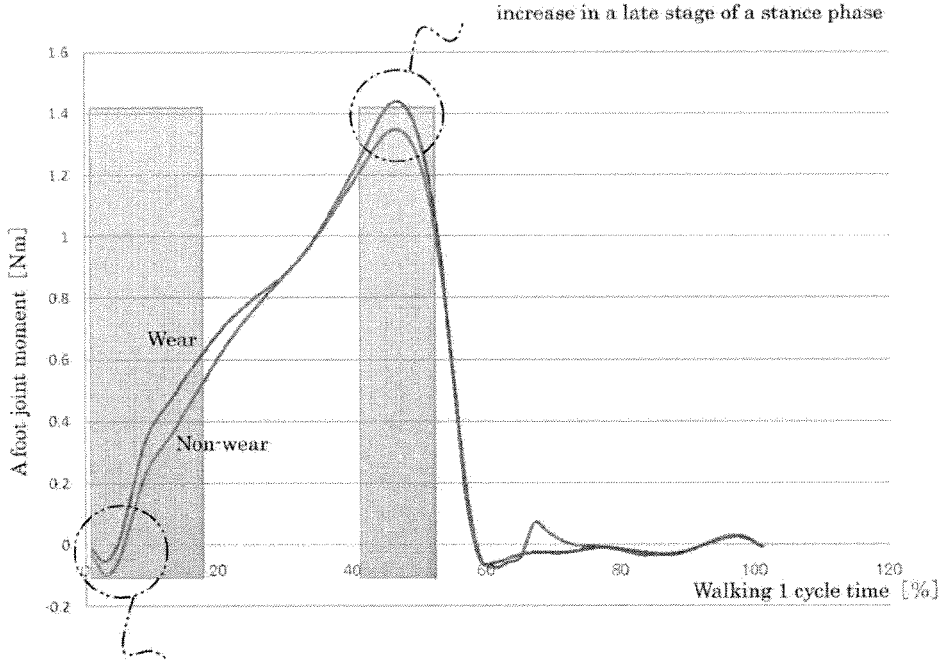
FIG. 6(b) is a graph showing the measurement results of a foot joint moment by three-dimensional motion analysis for verifying the operation and effects of the foot joint supporter shown in FIG. 1.

Further, as shown in FIG. 6(b), it can be found that with respect to a foot joint moment at the time of wearing, compared to a foot joint moment at the time of non-wearing, a dorsal flexion moment increases in the initial stage of a stance phase and an action to absorb an impact from the ground (a floor) by the foot joint supporter 10 works. Further, it can be found that with respect to a foot joint moment at the time of wearing, compared to a foot joint moment at the time of non-wearing, a plantar flexion moment increases in the late stage of a stance phase and the action of takeoff (a propulsive force in walking) by the foot joint supporter 10 works. That is, it can be found that since the foot joint supporter 10 increases a foot joint moment of a wearer, it is possible to improve a walking function of the wearer and also prevent the fatigue of the triceps surae muscle.

In the second experiment, in a case where the foot joint supporters 10 are worn on the right ankles of three test subjects (healthy adult males, average age: 29±3.6-year-old, average height: 169.7±4.9 cm, average weight: 64.3±11.9 kg) (the time of wearing) and a case where the foot joint supporter 10 is not worn (the time of non-wearing), free walking was carried out 10 times and the maximum dorsal flexion angles of the foot joint and foot joint plantar flexion moments were compared by three-dimensional motion analysis.

Figure 7A:
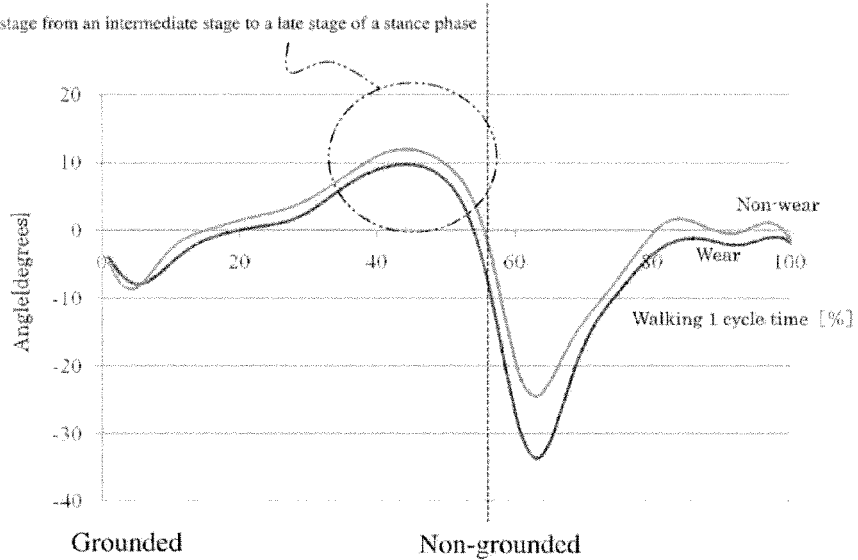
FIG. 7(a) is an explanatory diagram for describing a comparison range of the maximum dorsal flexion angle with respect to the measurement results of a foot joint angle by three-dimensional motion analysis for verifying the operation and effects of the foot joint supporter shown in FIG. 1.

The measurement results in the maximum dorsal flexion angle of the foot joint are the measured results of the maximum dorsal flexion angle of the foot joint of each test subject in a stage (a range surrounded by a two-dot chain line shown in FIG. 7(a)) from the intermediate stage to the late stage of a stance phase and are shown in Table 2 below and FIG. 8.

TABLE 2

|  | Test subject 1 (degree) | Test subject 2 (degree) | Test subject 3 (degree) | Average value (degree) |
| --- | --- | --- | --- | --- |
| Non-wear | 13.6 | 11.96 | 13.9 | 13.15 |
| Wear | 11.9 | 9.77 | 8.75 | 10.14 |

Figure 8A:
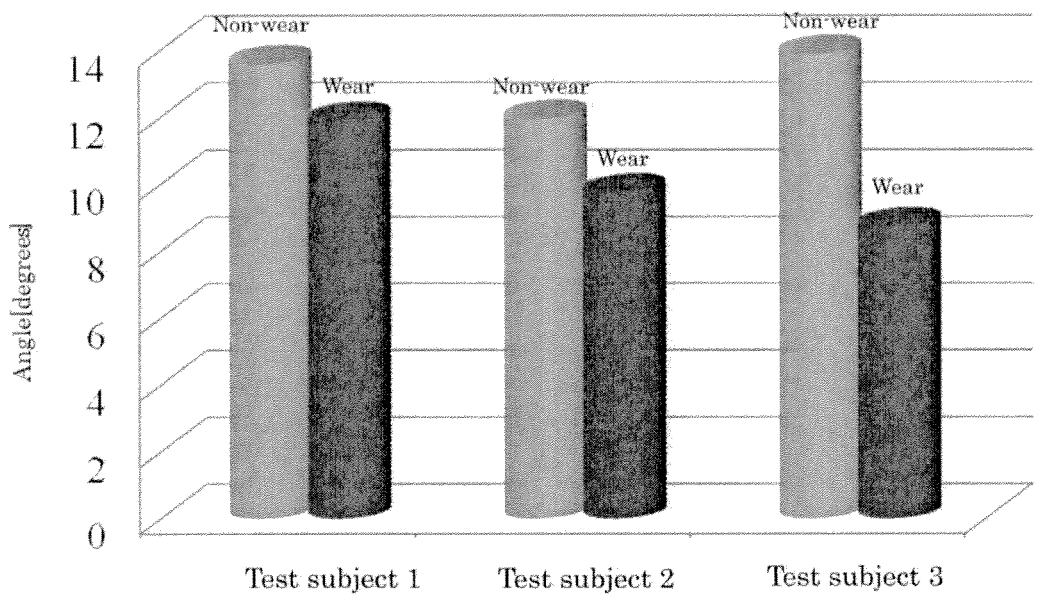
FIG. 8(a) is a graph showing the measurement results with respect to each test subject in the comparison range shown in FIG. 7(a)
Figure 8B:
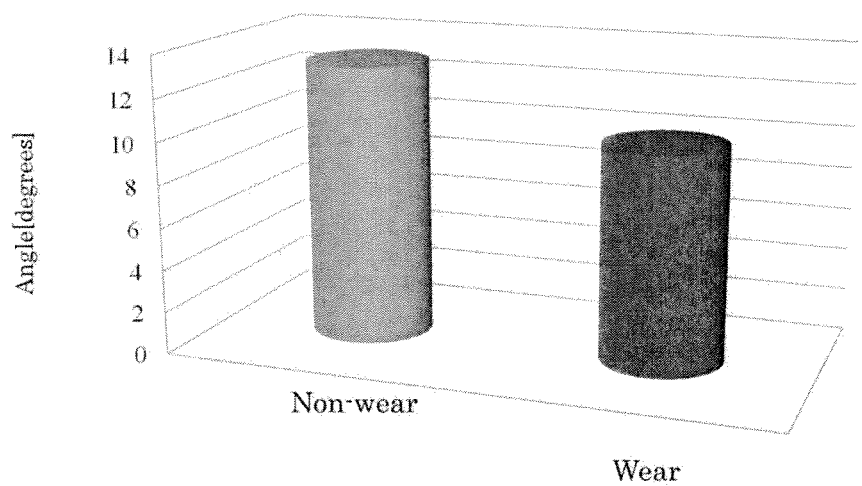
FIG. 8(b) is a graph showing the average value of the measurement results shown in FIG. 8(a).

As shown in Table 2 and FIG. 8, it can be found that in all the test subjects, at the time of wearing of the foot joint supporter 10, compared to the time of non-wearing, the maximum dorsal flexion angle of the foot joint becomes small. That is, it can be found that the foot joint supporter 10 controls (dorsal flexion braking) the maximum dorsal flexion angle of the foot joint in a wearer, so that the wearer can lean against the foot joint supporter 10 with respect to a dorsal flexion direction, and the foot joint supporter 10 becomes a power source for starting.

Figure 7B:
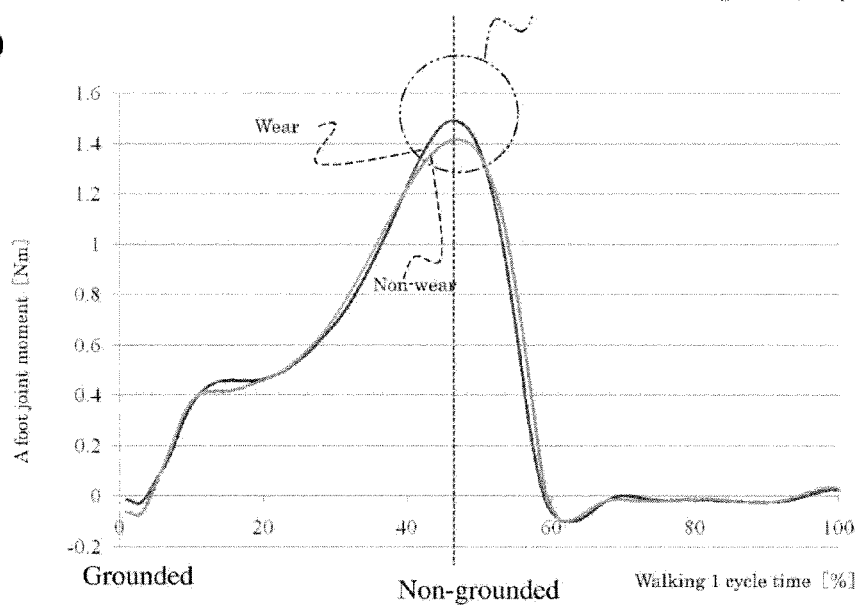
FIG. 7(b) is an explanatory diagram for describing a comparison range of a plantar flexion moment with respect to the measurement results of a foot joint moment by three-dimensional motion analysis for verifying the operation and effects of the foot joint supporter shown in FIG. 1.

Further, The measurement results in a foot joint plantar flexion moment are the results in which the integrated value of the foot joint plantar flexion moment of each test subject in the late stage (a range surrounded by a two-dot chain line shown in FIG. 7(b)) of a stance phase is normalized by the weight of each test subject and are shown in Table 3 below and FIG. 9.

TABLE 3

|  | Test subject 1 (Nm/kg) | Test subject 2 (Nm/kg) | Test subject 3 (Nm/kg) | Average value (Nm/kg) |
| --- | --- | --- | --- | --- |
| Non-wear | 1.476 | 1.416 | 1.343 | 1.411666667 |
| Wear | 1.532 | 1.493 | 1.435 | 1.486666667 |

Figure 9A:
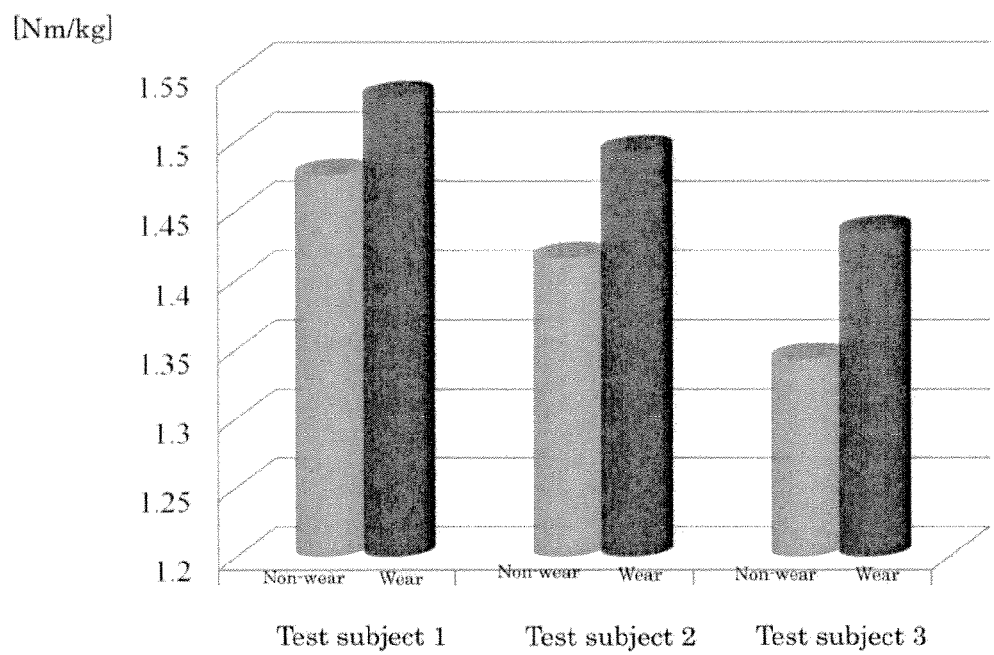
FIG. 9(a) is a graph showing the measurement results with respect to each test subject in the comparison range shown in FIG. 7(b)
Figure 9B:
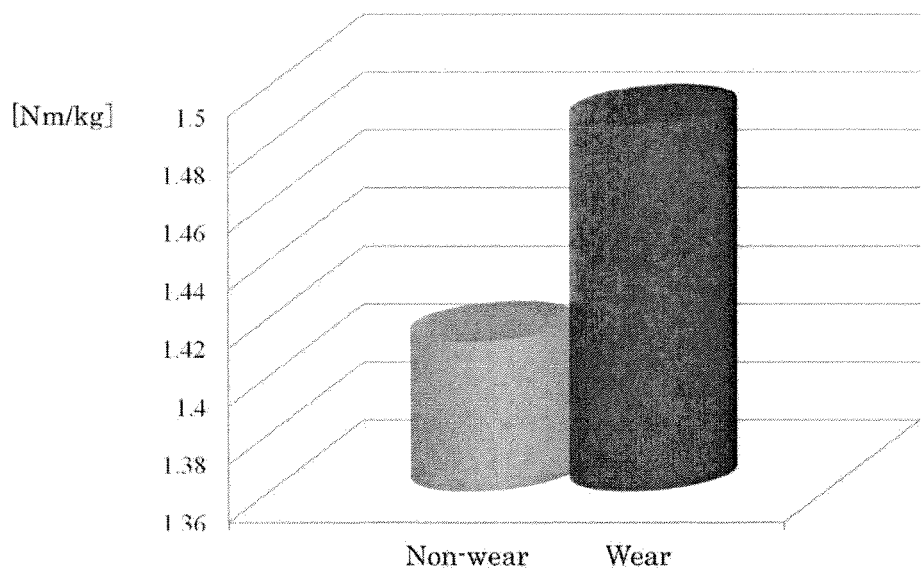
FIG. 9(b) is a graph showing the average value of the measurement results shown in FIG. 9(a).

As shown in Table 3 and FIG. 9, it can be found that in all the test subjects, at the time of wearing of the foot joint supporter 10, compared to the time of non-wearing, the foot joint plantar flexion moment (a propulsive force action) becomes large.

As described above, the foot joint supporter 10 has the operation and effects that can contribute to impact absorption in the initial stage of a stance phase and a propulsive force over a stage from the intermediate stage to the late stage of a stance phase and also allows the stability of the foot joint to be obtained by the left and right (varus and valgus) braking. Further, the foot joint supporter 10 has the operation and effects in which the foot joint supporter 10 assists the foot joint of a wearer, thereby being able to relieve Achilles' tendon pain, the fatigue and pain of the triceps surae muscle, and the pain of the outside (the ligament) of the foot joint.

(Second Embodiment of the Invention)

Figure 12A:
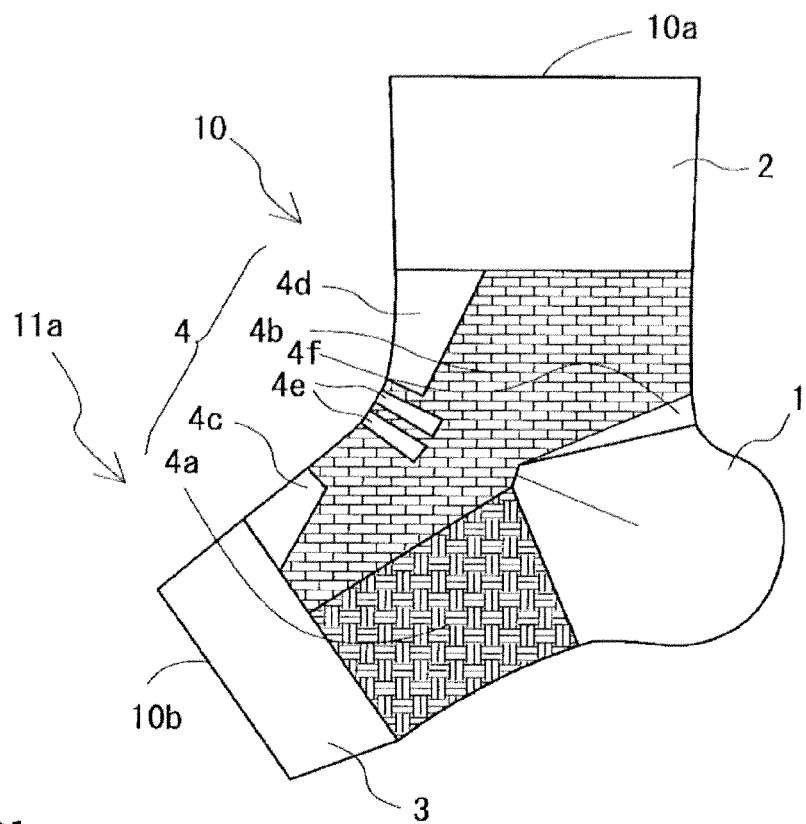
FIG. 12(a) is an explanatory diagram for describing the schematic configuration of the foot joint supporter related to the second embodiment.

FIG. 10(a) is a front view showing the schematic configuration of a foot joint supporter related to the second embodiment, FIG. 10(b) is a back view of the foot joint supporter shown in FIG. 10(a), FIG. 10(c) is a left side view of the foot joint supporter shown in FIG. 10(a), FIG. 10(d) is a right side view of the foot joint supporter shown in FIG. 10(a), FIG. 10(e) is a plan view of the foot joint supporter shown in FIG. 10(a), and FIG. 10(f) is a bottom view of the foot joint supporter shown in FIG. 10(a). FIG. 12(a) is an explanatory diagram for describing the schematic configuration of the foot joint supporter related to the second embodiment. In FIGS. 10 and 12(a), the same symbol as that in FIGS. 1 to 3 denotes the same or equivalent section, and explanation thereof is omitted.

The figure eight section 4 is provided with a third buffer section 4f which is knitted at the boundary between the body section 12 and the base fabric section 1 (the heel shaping section) in the foot joint supporter 10. The third buffer section 4f is knitted such that the stretch resistance thereof in the length direction L of the foot joint supporter 10 is larger than the stretch resistance of the base fabric section 1 (the heel shaping section) in the length direction L of the foot joint supporter 10 and smaller than the stretch resistance of the supporting section 4b (the other knitted fabric of the figure eight section 4, which is adjacent to the third buffer section 4f) in the length direction L of the foot joint supporter 10.

In addition, in this embodiment, by making the third buffer section 4f be a 2-tuck stitch knitted fabric and making the supporting section 4b be a 2-tuck stitch-plating stitch knitted fabric, it is possible to make the stretch resistance of the third buffer section 4f in the length direction L of the foot joint supporter 10 small with respect to the supporting section 4b. Further, also in this embodiment, the third buffer section 4f may also be made of a mesh stitch knitted fabric.

That is, when the tension of the third buffer section 4f in the length direction L of the foot joint supporter 10 is set to be $F_{L4f}$, the third buffer section 4f has such a magnitude relation of $F_{L4b} > F_{L4f}$ that it has a weak tightening force in the length direction L of the foot joint supporter 10, compared to the supporting section 4b.

Further, by making the third buffer section 4f be a 2-tuck stitch knitted fabric and making the base fabric section 1 (the heel shaping section) be a plain stitch knitted fabric, it is possible to make the stretch resistance of the third buffer section 4f in the length direction L of the foot joint supporter 10 large with respect to the base fabric section 1 (the heel shaping section).

That is, the third buffer section 4f has such a magnitude relation of $F_{L4f} > F_{L1}$ that it has a strong tightening force in the length direction L of the foot joint supporter 10, compared to the base fabric section 1 (the heel shaping section).

In addition, the second embodiment is different from the first embodiment only in that the third buffer section 4f is newly disposed at the supporting section 4b, and except the operation and effects by the third buffer section 4f, which will be described later, the same operation and effects as those in the first embodiment are obtained.

The third buffer section 4f is a section corresponding to the Achilles' tendon of a wearer, becomes a knitted fabric that a tightening force by the supporting section 4b on the back face side of the body section 12 does not reach, and suppresses tightening on the Achilles' tendon of the wearer while maintaining a tightening force on the ankle by the figure eight section 4, thereby allowing a pain to be relieved.

(Third Embodiment of the Invention)

Figure 12B:
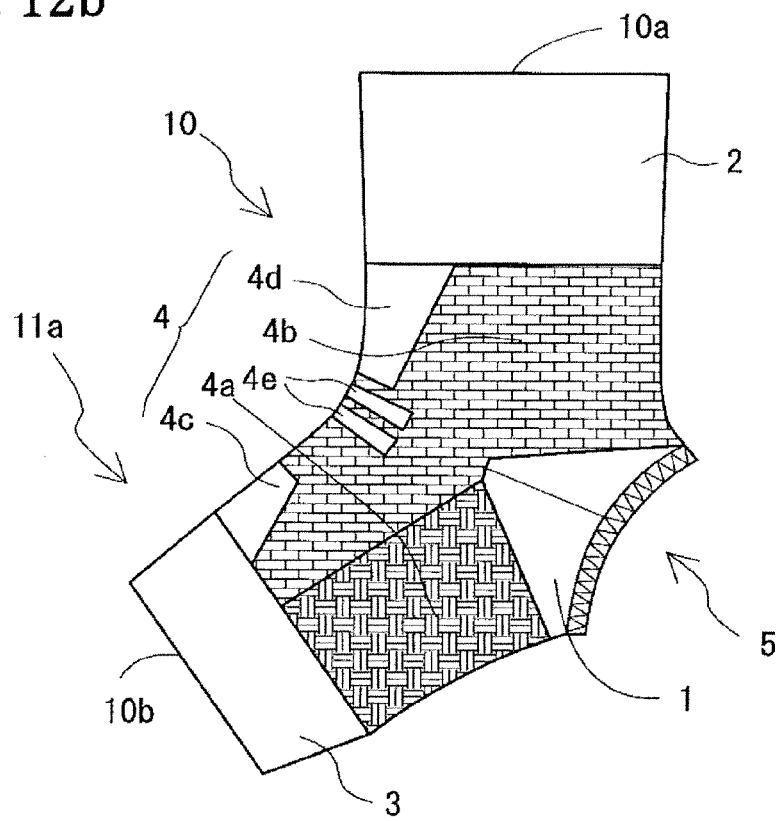
FIG. 12(b) is an explanatory diagram for describing the schematic configuration of the foot joint supporter related to the third embodiment.

FIG. 11(a) is a front view showing the schematic configuration of a foot joint supporter related to the third embodiment, FIG. 11(b) is a back view of the foot joint supporter shown in FIG. 11(a), FIG. 11(c) is a left side view of the foot joint supporter shown in FIG. 11(a), FIG. 11(d) is a right side view of the foot joint supporter shown in FIG. 11(a), FIG. 11(e) is a plan view of the foot joint supporter shown in FIG. 11(a), and FIG. 11(f) is a bottom view of the foot joint supporter shown in FIG. 11(a). FIG. 12(b) is an explanatory diagram for describing the schematic configuration of the foot joint supporter related to the third embodiment. In FIGS. 11 and 12(b), the same symbol as that in FIGS. 1 to 3 denotes the same or equivalent section, and explanation thereof is omitted.

A hole anchor section 5 is formed as an approximately circular through-hole in a site equivalent to the lower surface of the heel of a wearer, thereby exposing the heel of the wearer.

In addition, the hole anchor section 5 related to this embodiment is made by making a cut in the tubular knitted fabric which becomes the heel shaping section (the base fabric section 1), folding a cut edge back to the inside of the tubular knitted fabric, and sewing it by a sewing machine. However, the hole anchor section 5 may also be knitted by knitting without cutting out the tubular knitted fabric. In particular, it is preferable that a sewn section constituting the hole anchor section 5 be formed as a flexible bellows by using a sewing thread having high stretch property and increasing the number of stitching of a sewing machine, to reduce a pressing force which is imparted to the heel of a wearer.

The hole anchor section 5 exposes the heel of a wearer, whereby the foot joint supporter 10 is positioned with respect to the foot joint of the wearer and the rotational movement in the circumferential direction H or the parallel displacement in the length direction L of the foot joint supporter 10 is also suppressed, thereby being able to prevent a position shift.

Further, the hole anchor section 5 makes a portion of the heel of a wearer protrude therethrough, thereby constituting a pad by the protruding heel, and the pad improves the elastic force of the sole of the foot of a wearer, thereby being able to absorb an impact from the ground (a floor).

In addition, the third embodiment is different from the first embodiment only in that the hole anchor section which is formed as an approximately circular through-hole in a site equivalent to the lower surface of the heel of a wearer, thereby exposing the heel of the wearer, provided, and except the operation and effects by the hole anchor section 5, the same operation and effects as those in the first embodiment are obtained.

REFERENCE SIGNS LIST

1: base fabric section (heel shaping section)
2: first anchor section
3: second anchor section
4: figure eight section
4a: sole section
4b: supporting section
4c: first buffer section
4d: second buffer section
4e: thinly knitted section
4f: third buffer section
5: hole anchor section
10: foot joint supporter
10a: upper end
10b: lower end
11: foot section
11a: instep section
12: body section

The invention claimed is:

1. A foot joint supporter constructed from a tubular knitted fabric that is knitted by circular knitting, and adapted to come into close contact with a body surface of a wearer, thereby assisting a foot joint by improving stability thereof, the foot joint supporter comprising:
   a first anchor section which is knitted around an upper end of the tubular knitted fabric, the first anchor section adapted to surround portions corresponding to a tibia and a fibula in a vicinity of a malleolus of the wearer, the first anchor section allowing for the tubular knitted fabric to be tightened on a lower leg of the wearer;
   a second anchor section which is knitted around a lower end of the tubular knitted fabric, the second anchor section adapted to surround portions corresponding to a first metatarsal bone, a second metatarsal bone, a third metatarsal bone, a fourth metatarsal bone, and a fifth metatarsal bone in a vicinity of a metatarsophalangeal joint of the wearer, the second anchor section allowing for the tubular knitted fabric to be tightened on an instep and a sole of a foot of the wearer;
   a figure eight section which is knitted as a body section and a foot section excluding portions adapted to receive a heel and tiptoes of the wearer between the first anchor section and the second anchor section of the tubular knitted fabric and adapted to support a talocrural joint of the wearer; and
   a heel shaping section adapted to receive a heel of the wearer,
   wherein the foot section in the figure eight section includes an instep section adapted to receive an instep of the foot of the wearer and a sole section adapted to receive a sole of the foot of the wearer and is knitted in an area from the heel shaping section to the second anchor section, and
   the stretch resistance of the entire sole section in a length direction of the tubular knitted fabric is larger than the stretch resistance of the instep section in a length direction of the tubular knitted fabric.

2. The foot joint supporter according to claim 1, wherein the instep section in the figure eight section is provided with a first buffer section which is knitted in different knitting on a second anchor section side such that the stretch resistance of an area knitted in the different knitting in the length direction of the tubular knitted fabric is smaller than the stretch resistance of other areas in the instep section.

3. The foot joint supporter according to claim 2, wherein the first buffer section, is a mesh stitch knitted fabric.

4. The foot joint supporter according to claim 3, further comprising:
   a hole anchor section which exposes the heel of the wearer by forming an approximately circular through-hole in the heel shaping section.

5. The foot joint supporter according to claim 2, wherein the body section in the figure eight section is provided with a second buffer section which is knitted in different knitting on a front face side of the tubular knitted fabric such that the stretch resistance of an area knitted in the different knitting in the length direction of the tubular knitted fabric is smaller than the stretch resistance of other areas in the body section.

6. The foot joint supporter according to claim 5, wherein the first buffer section and/or the second buffer section is a mesh stitch knitted fabric.

7. The foot joint supporter according to claim 2, further comprising:
   a third buffer section which is knitted at a boundary between the body section in the figure eight section and the heel shaping section,
   wherein the stretch resistance of the third buffer section in the length direction of the tubular knitted fabric is larger than the stretch resistance of the heel shaping section in the length direction of the tubular knitted fabric and smaller than the stretch resistance of the other knitted fabric of the figure eight section, which is adjacent to the third buffer section, in the length direction of the tubular knitted fabric.

8. The foot joint supporter according to claim 2, wherein the figure eight section is knitted by additionally feeding another knitting yarn to ground knitting yarn such that elongation in the length direction of the tubular knitted fabric is small compared to elongation in a circumferential direction, and is provided with a thinly knitted section which includes the ground knitting yarn without feeding another knitting yarn, in the vicinity of a boundary between the body section and the foot section of the figure eight section on a front face side of the tubular knitted fabric and extends in the circumferential direction of the tubular knitted fabric.

9. The foot joint supporter according to claim 2, further comprising:

a hole anchor section which exposes the heel of the wearer by forming an approximately circular through-hole in the heel shaping section.

10. The foot joint supporter according to claim 1, wherein the body section in the figure eight section is provided with a second buffer section which is knitted in different knitting on a front face side of the tubular knitted fabric such that the stretch resistance of an area knitted in the different knitting in the length direction of the tubular knitted fabric is smaller than the stretch resistance of other areas in the body section.

11. The foot joint supporter according to claim 10, further comprising:

a third buffer section which is knitted at a boundary between the body section in the figure eight section and the heel shaping section, wherein the stretch resistance of the third buffer section in the length direction of the tubular knitted fabric is larger than the stretch resistance of the heel shaping section in the length direction of the tubular knitted fabric and smaller than the stretch resistance of the other knitted fabric of the figure eight section, which is adjacent to the third buffer section, in the length direction of the tubular knitted fabric.

12. The foot joint supporter according to claim 10, wherein the figure eight section is knitted by additionally feeding another knitting yarn to ground knitting yarn such that elongation in the length direction of the tubular knitted fabric is small compared to elongation in a circumferential direction, and is provided with a thinly knitted section which includes the ground knitting yarn without feeding another knitting yarn, in the vicinity of a boundary between the body section and the foot section of the figure eight section on a front face side of the tubular knitted fabric and extends in the circumferential direction of the tubular knitted fabric.

13. The foot joint supporter according to claim 10, further comprising:

a hole anchor section which exposes the heel of the wearer by forming an approximately circular through-hole in the heel shaping section.

14. The foot joint supporter according to claim 1, further comprising:

a third buffer section which is knitted at a boundary between the body section in the figure eight section and the heel shaping section, wherein the stretch resistance of the third buffer section in the length direction of the tubular knitted fabric is larger than the stretch resistance of the heel shaping section in the length direction of the tubular knitted fabric and smaller than the stretch resistance of the other knitted fabric of the figure eight section, which is adjacent to the third buffer section, in the length direction of the tubular knitted fabric.

15. The foot joint supporter according to claim 14, wherein the figure eight section is knitted by additionally feeding another knitting yarn to ground knitting yarn such that elongation in the length direction of the tubular knitted fabric is small compared to elongation in a circumferential direction, and is provided with a thinly knitted section which includes the ground knitting yarn without feeding another knitting yarn, in the vicinity of a boundary between the body section and the foot section of the figure eight section on the front face side of the tubular knitted fabric and extends in the circumferential direction of the tubular knitted fabric.

16. The foot joint supporter according to claim 14, wherein the third buffer section is a mesh stitch knitted fabric.

17. The foot joint supporter according to claim 14, further comprising:

a hole anchor section which exposes the heel of the wearer by forming an approximately circular through-hole in the heel shaping section.

18. The foot joint supporter according to claim 1, wherein the figure eight section is knitted by additionally feeding another knitting yarn to ground knitting yarn such that elongation in the length direction of the tubular knitted fabric is small compared to elongation in a circumferential direction, and is provided with a thinly knitted section which includes the ground knitting yarn without feeding another knitting yarn, in the vicinity of a boundary between the body section and the foot section of the figure eight section on a front face side of the tubular knitted fabric and extends in the circumferential direction of the tubular knitted fabric.

19. The foot joint supporter according to claim 17, further comprising:

a hole anchor section which exposes the heel of the wearer by forming an approximately circular through-hole in the heel shaping section.

20. The foot joint supporter according to claim 1, further comprising:

a hole anchor section which exposes the heel of the wearer by forming an approximately circular through-hole in the heel shaping section.

* * * * *